United States Patent [19]

Meek et al.

[11] Plant 4,716

[45] May 12, 1981

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 111,379

[22] Filed: Jan. 11, 1980

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar known by the cultivar name Heirloom and characterized as to uniqueness by the combined characteristics of flat capitulum form; daisy capitulum type; white ray floret color; diameter across face of capitulum ranging from 85 to 95 mm. at maturity; uniform nine week photoperiodic flowering response to short days; medium plant height when grown as a single stem cut spray; and semi-upright branching pattern.

3 Drawing Figures

1

The present invention comprises a new and distinct cultivar of *Chrysanthemum morifolium,* Ramat., hereinafter referred to by the cultivar name Heirloom.

Heirloom is a product of a planned breeding program which had the objective of creating new chrysanthemum cultivars with daisy capitulum type, white ray floret color, eight or nine week flowering response, and with the ability to produce commercially acceptable quality in year round cut mum programs. Such traits in combination were not present in previously available commercial cultivars.

Heirloom was originated from a hybridization made in a controlled breeding program in Barberton, Ohio in 1976. The female parent was a white daisy seedling (unnamed, No. 74079001) originated from a hybridization of two unnamed seedlings. The male parent of Heirloom was a white daisy seedling (unnamed, No. 74031001) originated from a hybridization of two unnamed seedlings.

Heirloom was discovered and selected as one flowering plant within the progeny of the stated cross by Jack M. Meek and William E. Duffett on Aug. 22, 1977 in a controlled environment in Salinas, Calif.

The first act of asexual reproduction of Heirloom was accomplished when vegetative cuttings were taken from the initial selection in February, 1978 in a controlled environment in Salinas, Calif. by a technician working under formulations established and supervised by Jack M. Meek and William E. Duffett. Horticultural examination of selected units initiated May 26, 1978 has demonstrated that the combination of characteristics as herein disclosed for Heirloom are firmly fixed and are retained through successive generations of asexual reproduction.

Heirloom has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Heirloom which in combination distinguish this chrysanthemum as a new and distinct cultivar:

2

(1) flat capitulum form, (2) daisy capitulum type, (3) white ray floret color, (4) yellow-green (immature) to yellow (mature) disc floret color, (5) diameter across face of capitulum ranging from 85 to 95 mm. at maturity, (6) uniform nine week photoperiodic flowering response to short days, (7) medium peduncle length, ranging from 100 to 175 mm., (8) medium plant height (requiring one to two long day weeks prior to short days to attain a flowered plant height of 65 to 75 cm. for May through October flowerings), and (9) semi-upright branching pattern.

Of the many commercial cultivars known to the present inventors, the most similar existing cultivar in comparison to Heirloom is the cultivar White Marble (unpatented). Reference is made to attached Chart A which compares certain characteristics of Heirloom to those same characteristics of White Marble. In general comparison to White Marble, Heirloom has larger diameter across face of capitulum and shorter peduncle length. The ray floret color, capitulum form, capitulum type, plant height and flowering response period of Heirloom are similar to those same characteristics of White Marble.

The accompanying photographic drawings show typical inflorescence and foliage characteristics of Heirloom, with colors being as nearly true as possible with illustrations of this type. Sheet 1 is a color photograph of Heirloom. Sheet 2 is a black and white photograph showing five views of the inflorescence of Heirloom. Sheet 3 is a black and white photograph showing the foliage of Heirloom at three stages of growth.

In the following description, color references are made to The Royal Horticultural Society (R.H.S.) Color Chart. The color values were determined between 1:30 and 2:00 P.M. on Oct. 22, 1979 under 100 foot-candle light intensity at Salinas, Calif.

Botanical classification: *Chrysanthemum morifolium,* Ramat., cv Heirloom.

I. Inflorescence:

A. *Capitulum* (*See Sheets 1 and 2 of drawings*).—Form: flat. Type: daisy. Diameter across face: 85 to 95 mm.

B. *Corolla of ray florets.*—General tonality (from a distance of three meters): white, 155-D. Color (abaxial): 155-D. Color (adaxial): 155-D.

C. *Corolla of disc florets.*—Color (abaxial): approximately 14-A. Color (adaxial): approximately 144-A (immature) to 14-A (mature).

D. *Reproductive organs.*—Androecium: present disc florets only; scant to numerous; moderate pollen. Gynoecium: present both ray and disc florets.

II. Plant:

A. *General appearance.*—Branching pattern: semi-upright. Height: medium, 60 to 70 cm. given no long days for May through October flowerings.

B. *Foliage* (*See Sheets 1 and 3*).—Color (abaxial): approximately 147-A. Color (adaxial): approximately 147-B. Shape: deeply lobed and slightly serrated.

CHART A

COMPARISON OF HEIRLOOM AND WHITE MARBLE

| | RAY FLORET | CAPITULUM FORM AND | DIAMETER ACROSS FACE OF |
|---|---|---|---|

CHART A-continued

COMPARISON OF HEIRLOOM AND WHITE MARBLE

| CULTIVAR | COLOR | TYPE | CAPITULUM |
|---|---|---|---|
| HEIRLOOM | White | Flat Daisy | 85 to 95 mm. |
| WHITE MARBLE | White | Flat Daisy | 70 to 85 mm. |

| CULTIVAR | PLANT HEIGHT | FLOWERING RESPONSE PERIOD | PEDUNCLE LENGTH |
|---|---|---|---|
| HEIRLOOM | Medium 60 to 70 cm. | 9 week | Medium 100 to 175 mm. |
| WHITE MARBLE | Medium 60 to 70 cm. | 9 week | Long 180 to 250 mm. |

COMPARISONS MADE OF PLANTS GROWN AS SINGLE STEM CUT SPRAYS IN SALINAS, CALIFORNIA

We claim:

1. A new and distinct cultivar of *Chrysanthemum morifolium,* Ramat., plant known by the cultivar name Heirloom and particularly characterized as to uniqueness by the combined characteristics of flat capitulum form; daisy capitulum type; white ray floret color; diameter across face of capitulum ranging from 85 to 95 mm. at maturity; uniform nine week photoperiodic flowering response to short days; medium peduncle length; medium plant height when grown as a single stem cut spray; and semi-upright branching pattern.

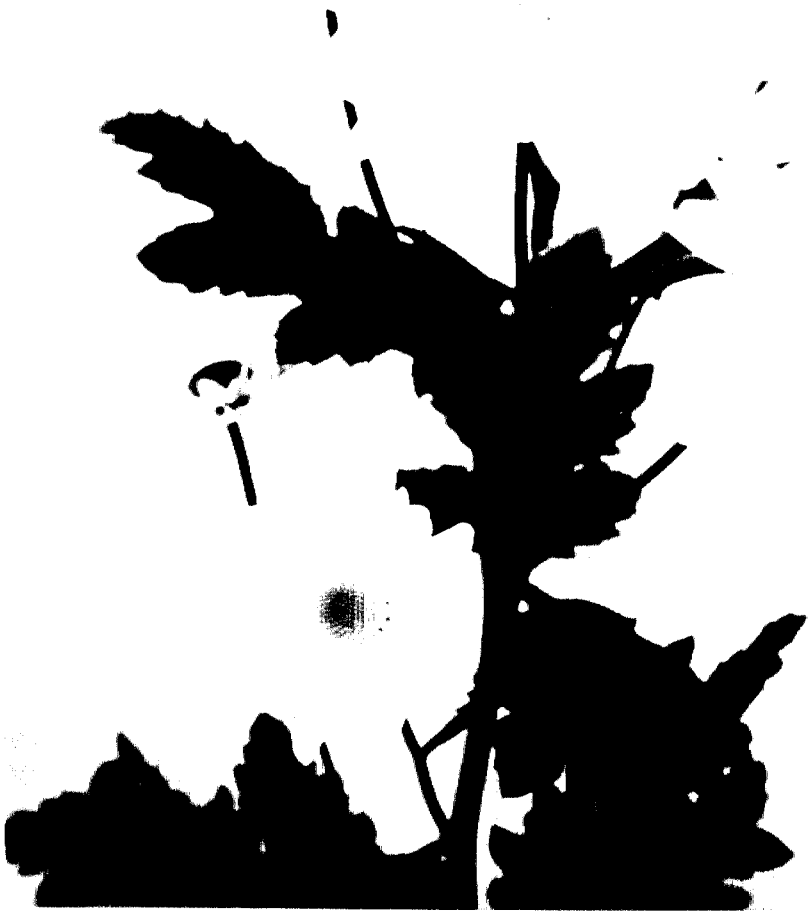

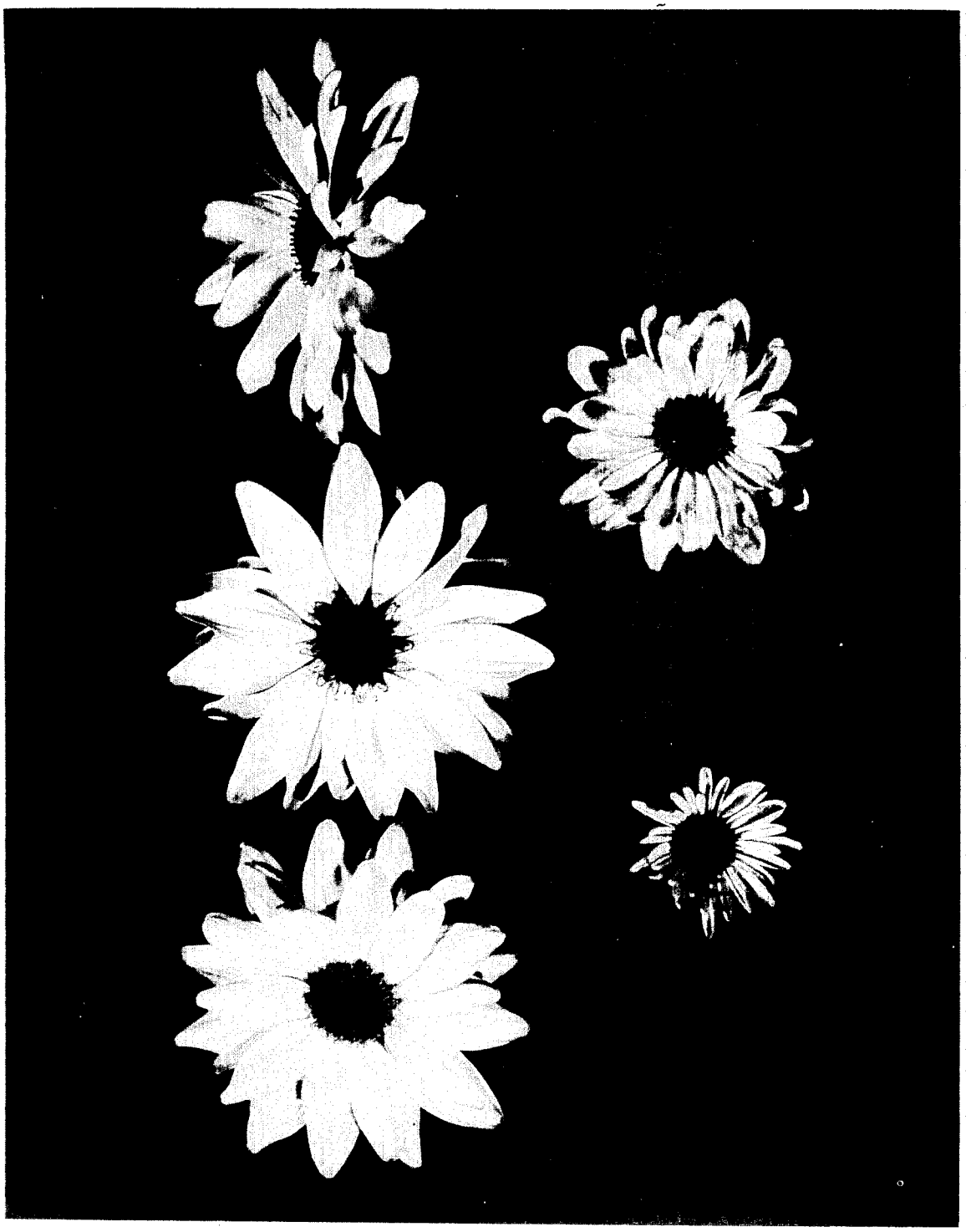

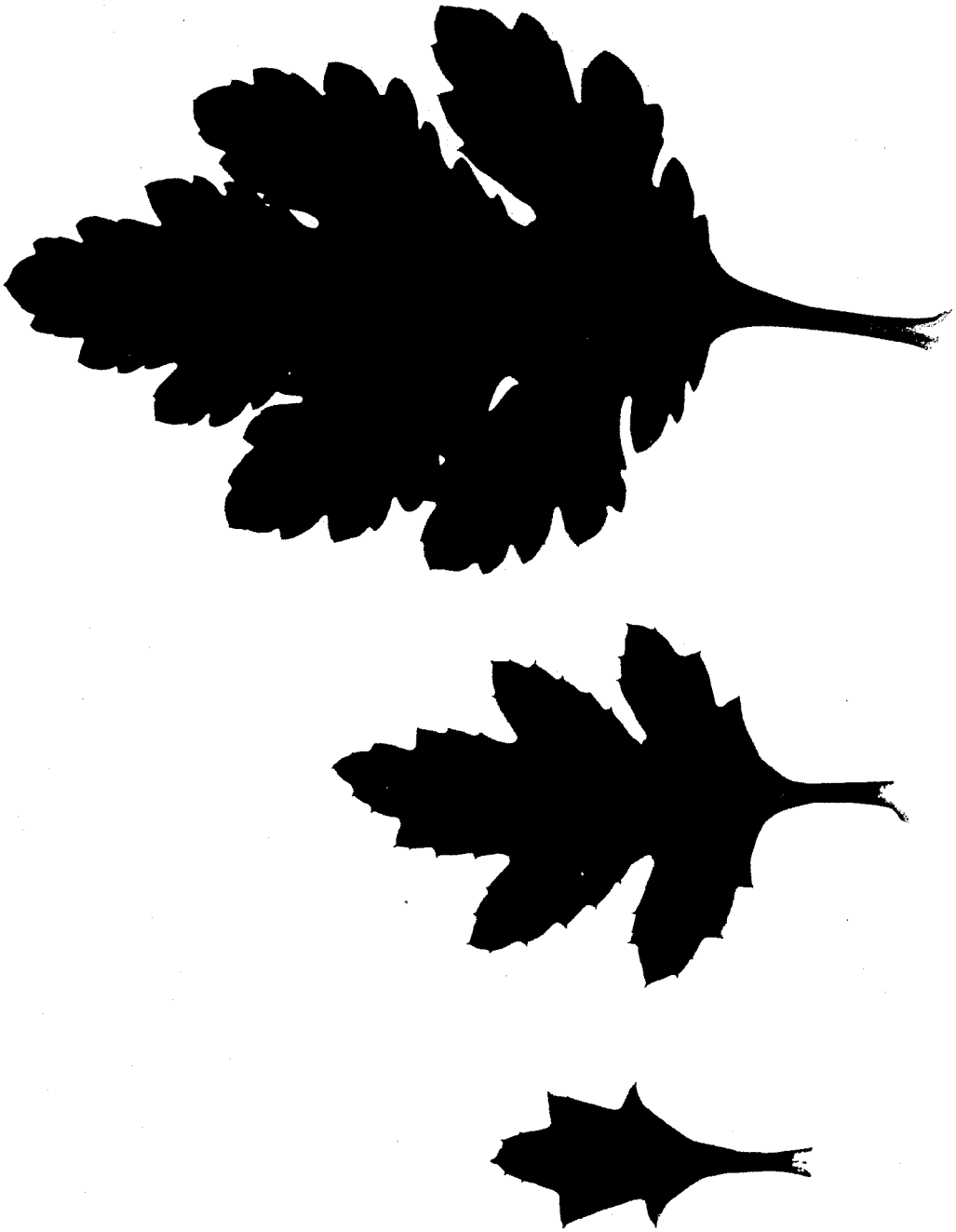

* * * * *